United States Patent
Nagatomo

(10) Patent No.: US 9,379,520 B2
(45) Date of Patent: Jun. 28, 2016

(54) SURFACE EMITTING LASER AND OPTICAL COHERENCE TOMOGRAPHY APPARATUS

(71) Applicant: CANON KABUSHIKI KAISHA, Tokyo (JP)

(72) Inventor: Yasuhiro Nagatomo, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/790,118

(22) Filed: Jul. 2, 2015

(65) Prior Publication Data

US 2016/0013618 A1     Jan. 14, 2016

(30) Foreign Application Priority Data

Jul. 11, 2014   (JP) .................................. 2014-142912

(51) Int. Cl.
*H01S 5/00*  (2006.01)
*H01S 5/183*  (2006.01)
(Continued)

(52) U.S. Cl.
CPC ........... *H01S 5/18366* (2013.01); *A61B 5/0066* (2013.01); *G01B 9/02001* (2013.01); *G01B 9/02091* (2013.01); *H01S 5/10* (2013.01); *H01S 5/1039* (2013.01); *H01S 5/12* (2013.01); *H01S 5/125* (2013.01); *H01S 5/183* (2013.01); *H01S 5/187* (2013.01); *H01S 5/1833* (2013.01); *H01S 5/18333* (2013.01); *H01S 5/18361* (2013.01); *H01S 5/18363* (2013.01)

(58) Field of Classification Search
CPC ............ H01S 5/18366; H01S 5/18363; H01S 5/1039; H01S 5/187; H01S 5/18361; H01S 5/183; H01S 5/12; H01S 5/125; H01S 5/1833; H01S 5/18333

USPC .................................... 372/20, 50.11, 50.124
See application file for complete search history.

(56) References Cited

U.S. PATENT DOCUMENTS

| | | | |
|---|---|---|---|
| 6,549,687 B1 | 4/2003 | Kochergin et al. | 385/12 |
| 7,869,483 B2 | 1/2011 | Uchida et al. | 372/99 |

(Continued)

FOREIGN PATENT DOCUMENTS

EP           2701249          2/2014

OTHER PUBLICATIONS

I.-S. Chung et al., "Broadband MEMS-Tunable High-Index-Contrast Subwavelength Grating Long-Wavelength VCSEL", *IEEE Journal of Quantum Electronics*, vol. 46, No. 9, pp. 1245-1253 (Sep. 2010).

(Continued)

*Primary Examiner* — Kinam Park
(74) *Attorney, Agent, or Firm* — Fitzpatrick, Cella, Harper & Scinto

(57) ABSTRACT

In order to provide a wavelength tunable surface emitting laser capable of improving a wavelength tuning efficiency, provided is a surface emitting laser, including: a first reflector; a semiconductor cavity including an active layer; and a second reflector, the first reflector, the semiconductor cavity, and the second reflector being formed in the stated order, a gap portion being formed between the first reflector and a semiconductor layer, a cavity length being tunable, in which the surface emitting laser has a high reflectivity structure formed between the gap portion and the semiconductor cavity, and an expression of "$(\lambda/2) \times m + \lambda/8 < L < (\lambda/2) \times m + 3\lambda/8$" is satisfied, where L is an optical thickness of the semiconductor cavity, m is an integer of 1 or larger, and $\lambda$ is a center wavelength of laser oscillation.

20 Claims, 6 Drawing Sheets

(51) Int. Cl.
*H01S 5/187* (2006.01)
*H01S 5/10* (2006.01)
*G01B 9/02* (2006.01)
*H01S 5/12* (2006.01)
*H01S 5/125* (2006.01)
*A61B 5/00* (2006.01)

(56) References Cited

U.S. PATENT DOCUMENTS

| | | | | |
|---|---|---|---|---|
| 8,249,126 B2 | 8/2012 | Nagatomo | | 372/99 |
| 2006/0268398 A1* | 11/2006 | Cole | | H01S 5/041 359/344 |
| 2008/0159468 A1* | 7/2008 | Chong | | A61B 5/0066 378/4 |
| 2009/0303487 A1* | 12/2009 | Bond | | G01N 21/39 356/437 |
| 2013/0278935 A1* | 10/2013 | Yamada | | G01B 9/02004 356/479 |
| 2014/0055790 A1* | 2/2014 | Inao | | H01S 5/06 356/479 |
| 2014/0176958 A1* | 6/2014 | Flanders | | H01S 5/06 356/479 |

OTHER PUBLICATIONS

EESR dated Dec. 10, 2015 from counterpart European patent application 15176035.2-1556 (in English).

* cited by examiner

SURFACE EMITTING LASER AND OPTICAL COHERENCE TOMOGRAPHY APPARATUS

BACKGROUND OF THE INVENTION

1. Field of the Invention

The present invention relates to a wavelength tunable surface emitting laser and an optical coherence tomography apparatus using the same.

2. Description of the Related Art

A wavelength tunable laser capable of changing a laser oscillation wavelength can be expected to be applied to various fields including communication, sensing, and imaging, and thus, is vigorously researched and developed in recent years.

As a kind of such a wavelength tunable laser, a structure is known that is so-called a MEMS-VCSEL in which a laser oscillation wavelength of a vertical cavity surface emitting laser (VCSEL) is controlled through a micro electro mechanical systems (MEMS) technology.

A VCSEL is generally formed by sandwiching an active layer between a pair of reflectors such as distribution Bragg reflectors (DBRs), and a laser is oscillated at a wavelength in accordance with a cavity length determined by an optical path length between the reflectors. In a MEMS-VCSEL, by mechanically moving a location of one of the reflectors, the cavity length can be changed to change the laser oscillation wavelength (see, for example, U.S. Pat. No. 6,549,687).

In a MEMS-VCSEL, an amount of change in laser oscillation wavelength with respect to an amount of change in reflector location is sometimes referred to as a wavelength tuning efficiency. It is known that the magnitude of the wavelength tuning efficiency is affected by the cavity length and a kind of surface coating ("Broadband MEMS-Tunable High-Index-Contrast Subwavelength Grating Long-Wavelength VCSEL", Il-Sug Chung et al., IEEE Journal of Quantum Electronics, Vol. 46, NO. 9, p. 1245-1253, 2010).

SUMMARY OF THE INVENTION

In order to enhance a wavelength sweep speed of a MEMS-VCSEL and to widen a wavelength tunable range, improvement of a wavelength tuning efficiency is desired.

In view of the problem described above, it is an object of the present invention to provide a wavelength tunable surface emitting laser capable of improving a wavelength tuning efficiency.

According to one embodiment of the present invention, there is provided a surface emitting laser, including:

a first reflector;
a semiconductor cavity including an active layer; and
a second reflector,
the first reflector, the semiconductor cavity, and the second reflector being formed in the stated order,
a gap portion being formed between the first reflector and the semiconductor cavity,
a cavity length being tunable,
in which the surface emitting laser has a high reflectivity structure formed between the gap portion and the semiconductor cavity, and
in which $(\lambda/2) \times m + \lambda/8 < L < (\lambda/2) \times m + 3\lambda/8$ is satisfied, where L is an optical thickness of the semiconductor cavity after conversion into an optical thickness in a case of no phase change in optical reflection at a first interface that is at a first reflector side of the semiconductor cavity and at a second interface that is at a second reflector side of the semiconductor cavity, m is an integer of 1 or larger, and $\lambda$ is a center wavelength of laser oscillation.

According to the one embodiment of the present invention, it is possible to provide the wavelength tunable surface emitting laser capable of improving the wavelength tuning efficiency.

Further features of the present invention will become apparent from the following description of exemplary embodiments with reference to the attached drawings.

DESCRIPTION OF THE EMBODIMENTS

Figure 1:
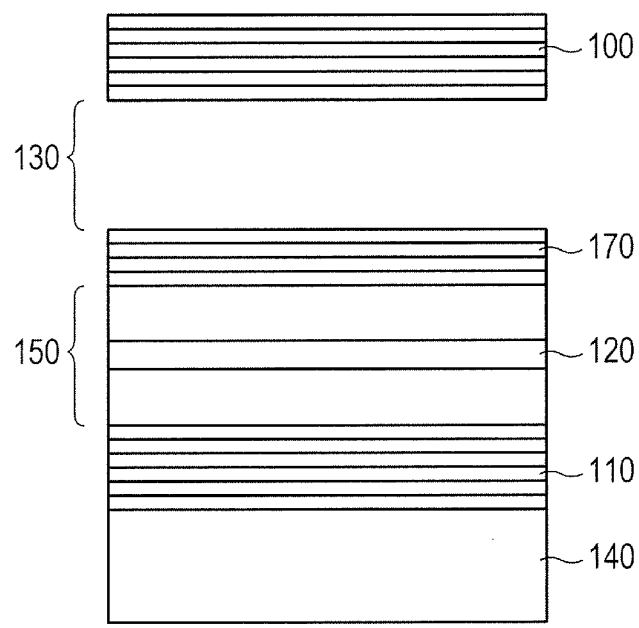
FIG. 1 is a schematic sectional view for illustrating a structure of a MEMS-VCSEL according to an embodiment of the present invention.

Preferred embodiments of the present invention will now be described in detail in accordance with the accompanying drawings.

Embodiment 1

A wavelength tunable vertical cavity surface emitting laser (VCSEL) according to an embodiment of the present invention is described in the following.

First, terms used herein are defined.

As used herein, a substrate side of a laser element is defined as a lower side and a side opposite to the substrate is defined as an upper side.

As used herein, a center wavelength is used to mean a wavelength at a center of a wavelength range of laser beams that can be emitted from a surface emitting laser. In other words, a center wavelength means a wavelength at a center between a shortest wavelength and a longest wavelength of lasers that can be oscillated. A wavelength of a laser that can be oscillated is determined by a range of change of a cavity length, a reflection band of a reflector, a gain band of an active layer, and the like. In designing, basically, the center wavelength is set, and then, structures of elements are determined accordingly.

As used herein, in a cavity including an upper reflector (a first reflector) and a lower reflector (a second reflector), a semiconductor layer located between a gap portion and the lower reflector is referred to as a semiconductor cavity, and an optical thickness thereof is referred to as a semiconductor cavity length. When an antireflection film or a high reflectivity structure is formed between the gap portion and the semiconductor cavity, the antireflection film and the high reflectivity structure are not included in the semiconductor cavity, and the semiconductor cavity length means an optical thickness without the antireflection film and the high reflectivity structure.

The antireflection film as used herein means a structure that reduces the reflectivity with respect to a reflectivity of optical reflection (Fresnel reflection) caused by a difference between a refractive index of a main material that forms the semiconductor cavity and a refractive index of the gap portion when light enters the gap portion side from the semiconductor cavity. Exemplary antireflection films include a layer formed of a material having an intermediate refractive index between the refractive index of the main material forming the semiconductor cavity and the refractive index of the gap portion, so as to have an optical thickness that is an odd multiple of $\lambda/4$, where $\lambda$ is the center wavelength. Further, it is also possible to inhibit reflection in a wider wavelength range by forming the antireflection film of a multilayer film.

On the other hand, the high reflectivity structure means a structure that works oppositely to the antireflection film, that is, a structure that increases the reflectivity with respect to the reflectivity of the optical reflection (Fresnel reflection) caused by the difference between the refractive index of the main material that forms the semiconductor cavity and the refractive index of the gap portion. Exemplary high reflectivity structures include a structure in which two kinds of layers having different refractive indices are stacked so that an optical thickness of each of the layers is an odd multiple of $\lambda/4$ and a total number of the layers is two or more. Specifically, it is preferred that the high reflectivity structure have a reflectivity of 50% or more at the center wavelength. It is more preferred that the high reflectivity structure have a reflectivity of 60% or more at the center wavelength. It is most preferred that the high reflectivity structure have a reflectivity of 70% or more at the center wavelength.

Figure 5A:
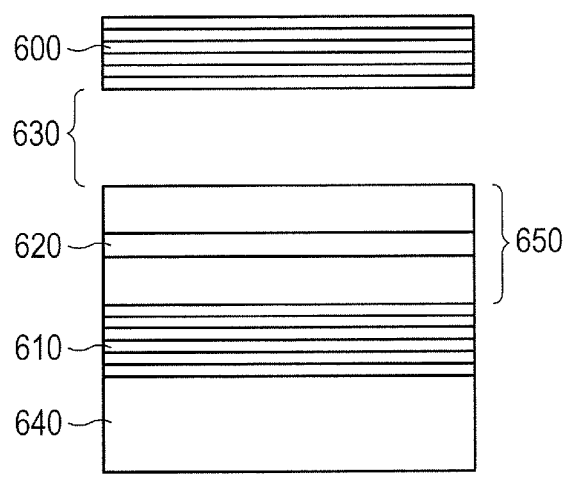
FIG. 5A, FIG. 5B and FIG. 5C are schematic sectional views for illustrating structures of MEMS-VCSELs of comparative examples.

FIG. 5A is a schematic sectional view of a typical MEMS-VCSEL.

The MEMS-VCSEL illustrated in FIG. 5A is formed of a GaAs-based compound semiconductor. The MEMS-VCSEL is set to have a center wavelength of 1,065 nm, and is designed so that the wavelength is tunable around the center wavelength. A cavity structure in which an active layer 620 is placed between an upper reflector 600 and a lower reflector 610 is placed on a substrate 640. A gap portion 630 is formed in the cavity structure, specifically, between the upper reflector 600 and the active layer 620, so that the upper reflector 600 can be driven. As the upper and lower reflectors, distribution Bragg reflectors (DBRs) each formed of a multilayer film are used.

An optical thickness between the upper reflector 600 and the lower reflector 610 is referred to as a cavity length. Through the movement of the upper reflector 600 in an optical axis direction, a length of the gap portion 630 can be changed to change the cavity length, which is accompanied by a change in laser oscillation wavelength. Note that, the optical axis direction as used herein means a direction of a line connecting the upper reflector and the lower reflector, and is a direction perpendicular to a principal plane of the substrate. In the FIG. 5A to 5C, the optical axis direction corresponds to a vertical direction.

A semiconductor layer 650 that is formed between the lower reflector 610 and the gap portion 630 and that includes the active layer 620 is referred to as a semiconductor cavity, and an optical thickness thereof is referred to as a semiconductor cavity length. In other words, the semiconductor cavity length is an optical path length between an interface between the lower reflector 610 and the semiconductor layer 650 and an interface between the gap portion 630 and the semiconductor layer 650. Note that, the cavity length of the entire cavity is a sum of the semiconductor cavity length and an optical thickness of the gap portion.

Figure 6:
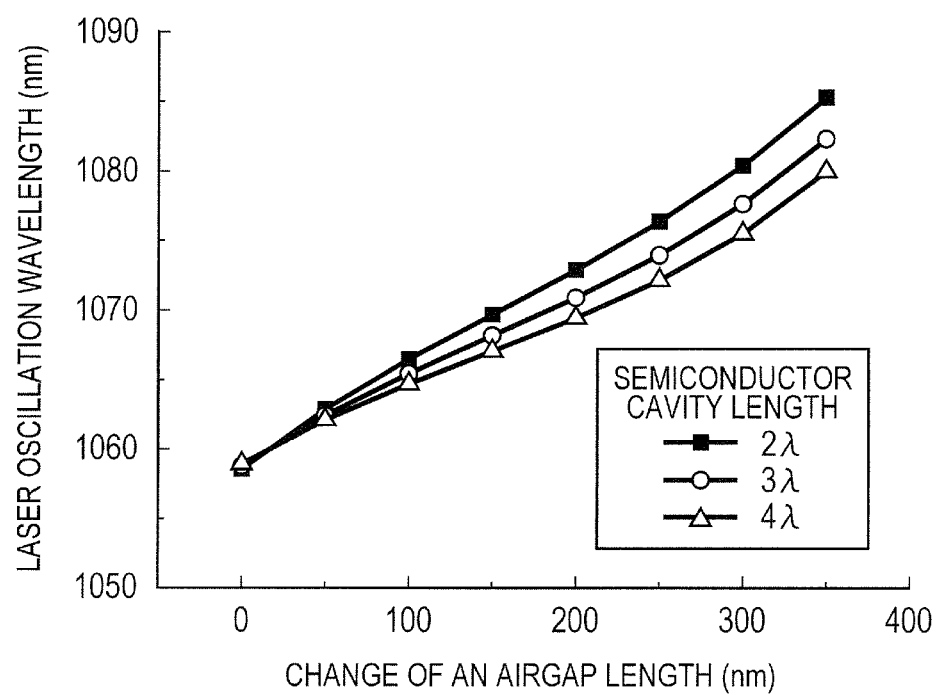
FIG. 6 is a graph for showing results of calculation exhibiting optical characteristics of MEMS-VCSELs of comparative examples.

FIG. 6 is a graph for showing results of calculation of a relationship between the gap portion length (airgap length) and the laser oscillation wavelength of the MEMS-VCSEL structure illustrated in FIG. 5A. In this case, the calculation is performed with regard to three kinds of structures having the semiconductor cavity length of $2\lambda$, $3\lambda$, and $4\lambda$, respectively, where $\lambda$ is the center wavelength.

From the results of the calculation, it can be seen that, as the semiconductor cavity length becomes larger, a gradient of the graph becomes smaller. The gradient of the graph represents a change ($\partial\lambda/\partial d_{air}$) in the laser oscillation wavelength ($\lambda$) relative to the gap portion length ($d_{air}$), which is hereinafter referred to as a wavelength tuning efficiency.

That the wavelength tuning efficiency is high is advantageous in the MEMS-VCSEL in the following point.

As the wavelength tuning efficiency becomes higher, an amount of displacement of the reflector necessary for changing an oscillation wavelength to a similar extent can be made smaller, and thus, a voltage necessary for mechanically driving the reflector and the like can be lowered. When the reflector is driven with a similar level of voltage, a structure having a larger spring constant and a higher resonance frequency can be adopted, which is advantageous to a high-speed wavelength sweep.

Further, increasing the wavelength tuning efficiency leads to broadening the longitudinal mode spacing. If the longitudinal mode spacing is narrow, mode hopping is caused, and the laser oscillation wavelength discontinuously hops or oscillation occurs simultaneously at a plurality of wavelengths, which is a cause of limiting a wavelength tunable width in a single mode. Through the broadening of the longitudinal mode spacing, this restriction can be removed.

Next, an effect of the wavelength tuning efficiency on the longitudinal mode spacing is described with reference to results of calculation shown in FIG. 7A and FIG. 7B.

Figure 7A:
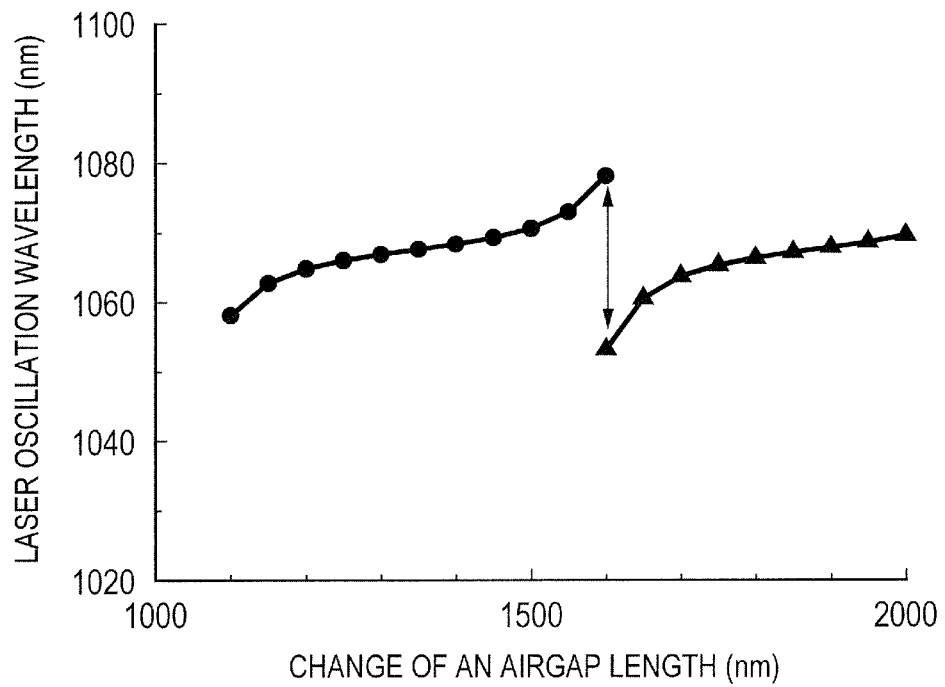
FIG. 7A and FIG. 7B are graphs for showing results of calculation for illustrating a relationship between a wavelength tuning efficiency and a longitudinal mode spacing.
Figure 7B:
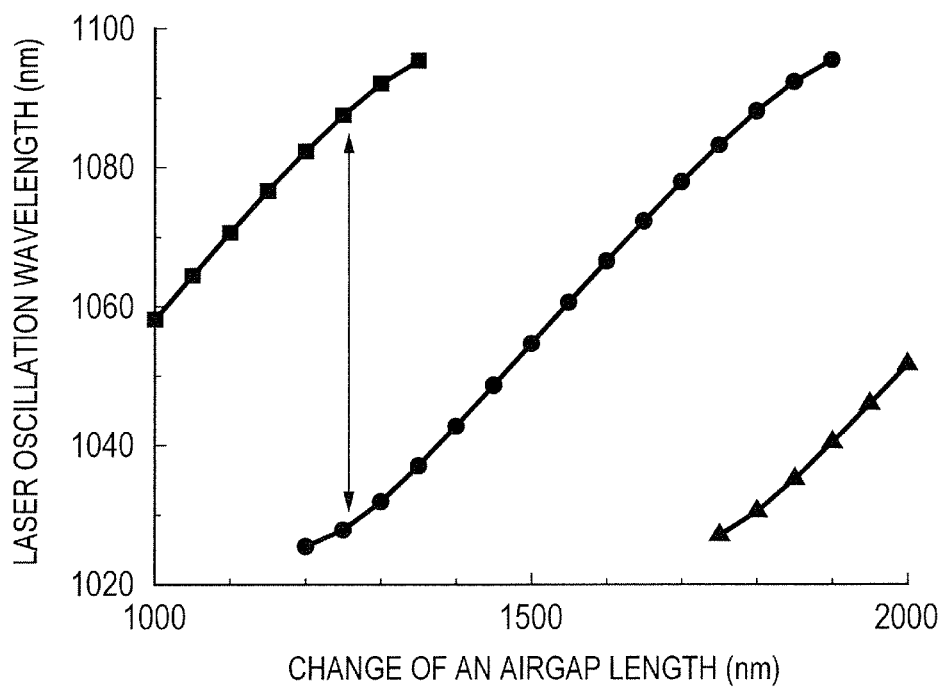

FIG. 7A and FIG. 7B are graphs for showing results of calculation with regard to two kinds of MEMS-VCSEL structures having different cavity structures. Both are MEMS-VCSELs that are designed so that the wavelength is tunable at a center wavelength of about 1,065 nm, but due to the difference in cavity structure, the wavelength tuning efficiency is different.

The wavelength tuning efficiency at around the center wavelength in FIG. 7A is about 0.015, and a wavelength spacing with a longitudinal mode of a next order is about 25 nm. On the other hand, the wavelength tuning efficiency at around the center wavelength in FIG. 7B is about 0.12, and a wavelength spacing with a longitudinal mode of a next order is about 60 nm.

In this way, it can be confirmed that, as the wavelength tuning efficiency is higher, the longitudinal mode spacing tends to be broadened.

As described with reference to the results of calculation shown in FIG. 6, it is known that the magnitude of the wavelength tuning efficiency depends on the semiconductor cavity length. In order to increase the wavelength tuning efficiency, it is effective to reduce the semiconductor cavity length, but in reality, there is a limit.

In particular, in the case of a structure in which the laser is oscillated through current injection, it is necessary to form a layer for diffusing and narrowing an electric current, and thus, compared with a structure in which the laser is oscillated through optical excitation, it is necessary to increase the semiconductor cavity length, and it is difficult to increase the wavelength tuning efficiency.

As an example to increase the wavelength tuning efficiency through a measure other than reducing the semiconductor cavity length, there is generally known a structure in which an antireflection (AR) film is formed at an interface between the gap portion and the semiconductor cavity. On the other hand, it is also generally known that, when a structure for increasing the reflectivity such as a distribution Bragg reflector (DBR) is formed at the interface between the gap portion and the semiconductor cavity, the wavelength tuning efficiency is lowered ("Broadband MEMS-Tunable High-Index-Contrast Subwavelength Grating Long-Wavelength VCSEL", Il-Sug Chung et al., IEEE Journal of Quantum Electronics, Vol. 46, NO. 9, p. 1245-1253, 2010).

This is described with reference to FIG. 5A to FIG. 5C and FIG. 8.

Figure 5B:
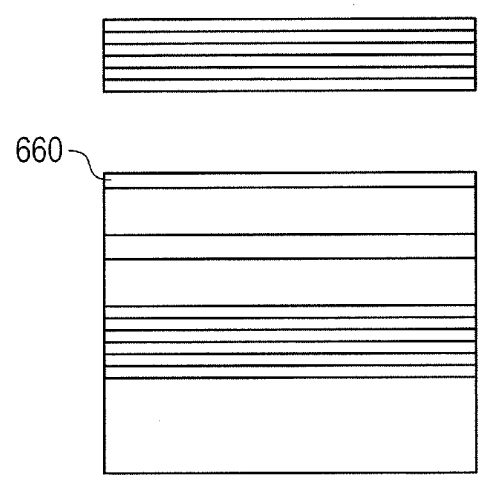
Figure 5C:
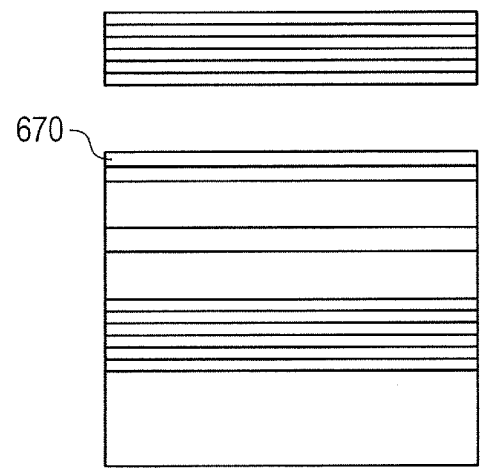

FIG. 5A to FIG. 5C are schematic sectional views of GaAs-based MEMS-VCSEL structures that are formed so that the wavelength is tunable at about 1,065 nm.

The structure illustrated in FIG. 5A is a basic structure with nothing formed at the interface between the gap portion 630 and the semiconductor cavity 650.

A structure illustrated in FIG. 5B is a structure in which an AlAs oxide layer at an optical thickness of a ¼ wavelength is added as an antireflection (AR) film 660 to the interface between the gap portion 630 and the semiconductor cavity 650 of the structure illustrated in FIG. 5A.

A structure illustrated in FIG. 5C is a structure in which a DBR 670 including a stacked pair of a GaAs layer and an AlAs oxide layer each at an optical thickness of a ¼ wavelength is added to the interface between the gap portion 630 and the semiconductor cavity 650 of the structure illustrated in FIG. 5A.

In each of the structures illustrated in FIG. 5A to FIG. 5C, the semiconductor cavity length except for the antireflection film and the DBR is designed to be $3.00\lambda$ when the center wavelength of 1,065 nm is $1.00\lambda$.

Note that, in each of the structures illustrated in FIG. 5A to FIG. 5C, calculated values of the reflectivity at the interface of the semiconductor cavity 650 on the gap portion 630 side when light having a wavelength of 1,065 nm enters the gap portion 630 side from the semiconductor cavity 650 are as follows. In the structure illustrated in FIG. 5A, the reflectivity at the interface of the semiconductor cavity 650 on the gap portion 630 side, that is, at the interface between the semiconductor cavity 650 and the gap portion 630, is 28.4%. In the structure illustrated in FIG. 5B, the reflectivity at the interface of the semiconductor cavity 650 on the gap portion 630 side, that is, at the interface between the semiconductor cavity 650 and the antireflection film 660, is 0.1%. In the structure illustrated in FIG. 5C, the reflectivity at the interface of the semiconductor cavity 650 on the gap portion 630 side, that is, at the interface between the semiconductor cavity 650 and the DBR 670 (high reflectivity structure), is 73.5%.

Figure 8:
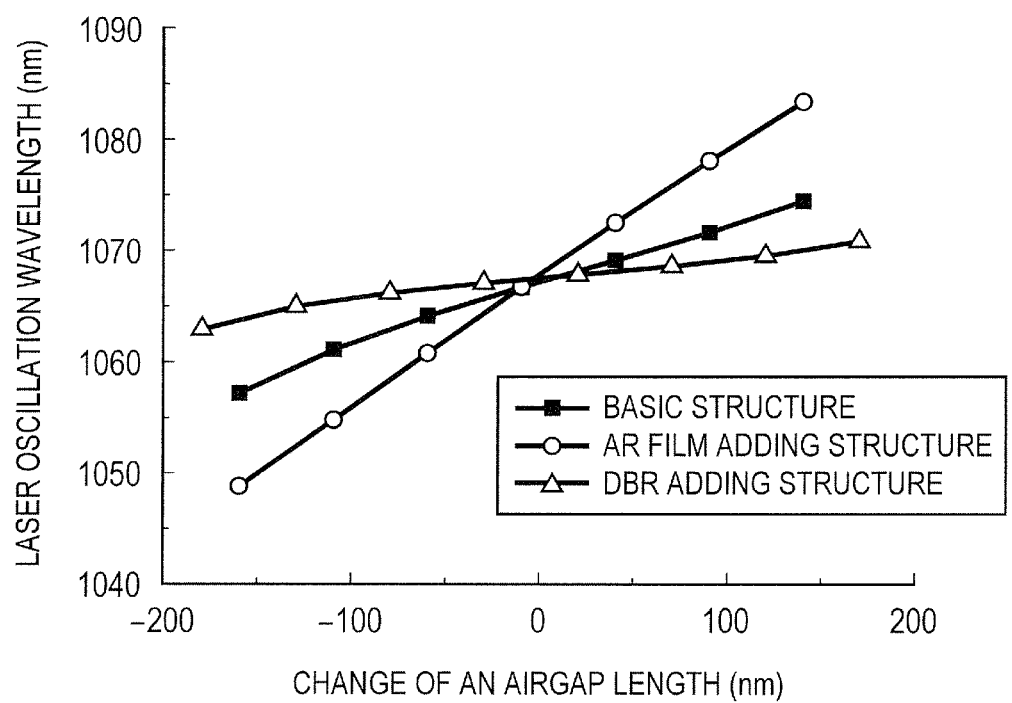
FIG. 8 is a graph for showing results of calculation exhibiting optical characteristics of the MEMS-VCSELs of the comparative examples.

FIG. 8 is a graph for showing results of calculation exhibiting a relationship between an amount of change of the gap portion length (airgap length) and the laser oscillation wavelength with respect to the wavelength of about 1,065 nm with regard to each of the structures illustrated in FIG. 5A to FIG. 5C.

It is confirmed that, compared with the basic structure (corresponding to FIG. 5A), the structure having the AR film added thereto (corresponding to FIG. 5B) has a higher wavelength tuning efficiency, while the structure having the DBR added thereto (corresponding to FIG. 5C) has, in reverse, a lower wavelength tuning efficiency.

As described above, it has been generally known that the wavelength tuning efficiency can be improved by reducing the cavity length of the MEMS-VCSEL as much as possible or by forming an AR film at the interface between the gap portion and the semiconductor cavity.

However, in order to realize a MEMS-VCSEL capable of changing the wavelength more quickly and over a wider range, further improvement of the wavelength tuning efficiency is desired.

In a structure to which the present invention is applied, by combining selection of a semiconductor cavity length different from that of the related-art structures and an increase in reflectivity at the interface between the gap portion and the semiconductor cavity, the wavelength tuning efficiency can be increased compared with that of the related-art structures.

Specifically, by forming the MEMS-VCSEL so that the semiconductor cavity length is close to $(\lambda/2) \times m + \lambda/4$ and forming a high reflectivity structure at the interface between the gap portion and the semiconductor cavity, the effect described above can be obtained (where m is an integer of 1 or larger, and $\lambda$ is a center wavelength, which also applies to the following description).

A high reflectivity structure as used herein is a structure formed so that the reflectivity is higher than that of the optical reflection caused at the interface by the difference between the refractive index of a semiconductor material as the main material that forms the semiconductor cavity and the refractive index of the gap portion. Exemplary high reflectivity structures include a structure in which at least one pair of a high refractive index layer formed of a material having a relatively high refractive index and a low refractive index layer formed of a material having a relatively low refractive index are stacked. It is more preferred that the high reflectivity structure be a multilayer film structure in which a layer formed of a material having a relatively high refractive index and a layer formed of a material having a relatively low refractive index are alternately stacked such as in a DBR so that an optical thickness of each of the layers is an odd multiple of $\lambda/4$, where $\lambda$ is the center wavelength.

Further, the semiconductor cavity is a stacked body of all semiconductor layers placed between the high reflectivity structure and the lower reflector.

An exemplary MEMS-VCSEL to which the present invention is applied is described with reference to FIG. 1.

An upper reflector 100, a gap portion 130, a high reflectivity structure 170, a semiconductor cavity 150 including an active layer 120, a lower reflector 110, and a substrate 140 are placed in the stated order from the top. An optical thickness of the semiconductor cavity 150 is referred to as the semiconductor cavity length. In other words, the semiconductor cavity length is an optical path length between an interface between the high reflectivity structure 170 and the semiconductor cavity 150 and an interface between the semiconductor cavity 150 and the lower reflector 110.

The structure to which the present invention is applied is formed so that the semiconductor cavity length is $(\lambda/2) \times m + \lambda/4$, where $\lambda$ is the center wavelength.

In the present invention, the MEMS-VCSEL may be of a current injection type in which light is emitted through current injection into the active layer 120 by an electrode (not shown), or may be of an optical excitation type in which excitation light is irradiated to the active layer 120 by an external light source (not shown).

Further, the upper reflector 100 is driven in a thickness direction of the MEMS-VCSEL by a static electric force generated by applying a voltage between electrodes (not shown).

Note that, the semiconductor cavity length is herein converted to that in the case of free end reflection in which there is no phase change at the upper and lower interfaces of the semiconductor cavity in the optical reflection. Conversion means that, when there is a phase change in optical reflection at the upper and lower interfaces of the semiconductor cavity, the optical thickness of the semiconductor cavity length is caused to be an optical thickness taking into consideration an amount of the phase change. A specific method for the conversion is described in, for example, a third paragraph of "Broadband MEMS-Tunable High-Index-Contrast Subwavelength Grating Long-Wavelength VCSEL", Il-Sug Chung et al., IEEE Journal of Quantum Electronics, Vol. 46, NO. 9, p. 1245-1253, 2010.

When there is a phase change in reflection, the effective optical path varies accordingly, and thus, it is necessary to adjust the actual semiconductor cavity length. For example, in the case of fixed end reflection when the phase change in reflection is $\pi$, the effective optical path is shifted by $\lambda/2$ from that in the case of free end reflection. In order to make an optical path length of $\lambda/2$ through a round trip of the cavity, it is necessary to change the cavity length by $\lambda/4$.

For example, in the case of fixed end reflection at only any one of the upper and lower interfaces of the semiconductor cavity, the semiconductor cavity length suitable for the present invention is $(\lambda/2) \times m + \lambda/4$ minus $\lambda/4$ (or plus $\lambda/4$), which is $(\lambda/2) \times m$ (or $(\lambda/2) \times (m+1)$).

Optical reflection at the upper and lower interfaces of the semiconductor cavity is herein configured to be free end reflection unless otherwise specified.

Note that, generally, when light enters a layer formed of a material having a low refractive index from a layer formed of a material having a high refractive index, the optical reflection at the interface therebetween is free end reflection. On the other hand, when light enters a layer formed of a material having a high refractive index from a layer formed of a material having a low refractive index, the optical reflection at the interface therebetween is fixed end reflection.

Further, in the case of a multilayer film, lights reflected from the respective interfaces are composed, and thus, there are cases in which the reflection can be neither clear free end reflection nor clear fixed end reflection. In the case of a DBR, basically, when a layer nearest to an active layer of the DBR has a refractive index that is higher than that of a medium in an incident side layer in contact with the layer, the reflection is fixed end reflection. On the other hand, when the layer nearest to the active layer of the DBR has a refractive index that is lower than that of the medium in the incident side layer in contact with the layer, the reflection is free end reflection. However, as the optical thicknesses of the respective layers in the DBR are shifted from $\lambda/4$, the reflection gradually deviates from clear fixed end reflection or clear free end reflection. Further, in the case of, for example, a DBR in which the high refractive index layer is thicker than $\lambda/4$ and the low refractive index layer is thinner than $\lambda/4$ such as a thickness modulated DBR, the reflection is neither free end reflection nor fixed end reflection even at the center wavelength.

Based on this point, the MEMS-VCSEL according to the present invention is formed so that the semiconductor cavity length is $(\lambda/2) \times m + \lambda/4$, where $\lambda$ is the center wavelength, after conversion into the case of free end reflection.

As the upper reflector 100 and the lower reflector 110, distribution Bragg reflectors (DBRs) each formed of a multilayer film are used. A region sandwiched between the upper reflector 100 and the lower reflector 110 is a cavity in which an optical standing wave is formed. The upper reflector 100 is movable in the optical axis direction (vertical direction in FIG. 1). By changing a length of the gap portion 130 (hereinafter referred to as airgap length), the cavity length is changed to change the laser oscillation wavelength.

Figure 2:
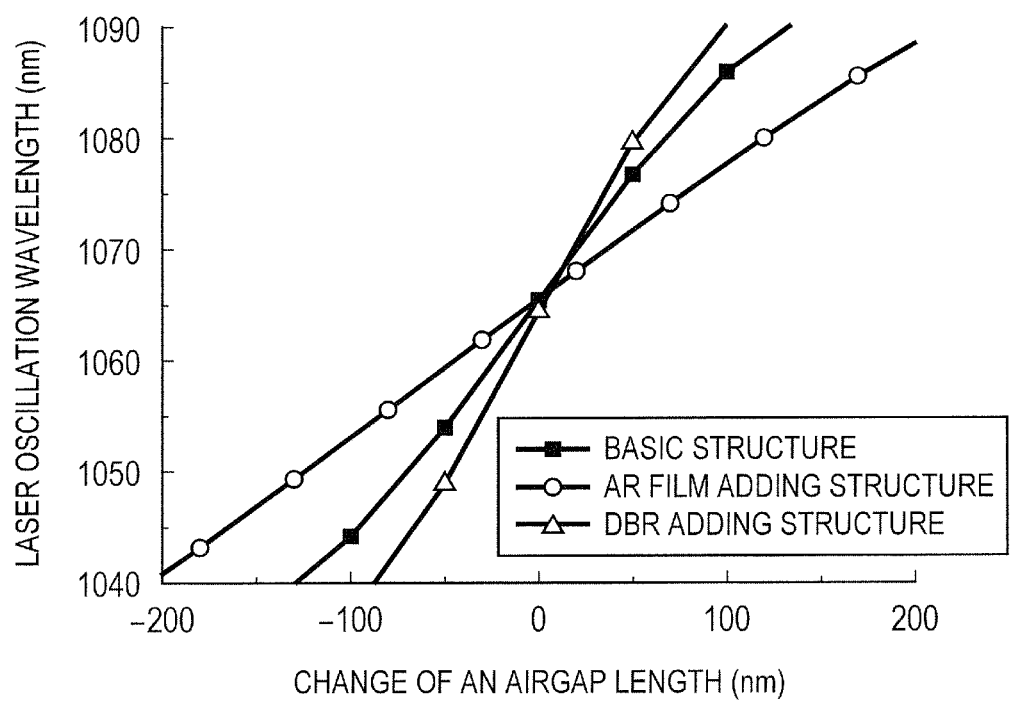
FIG. 2 is a graph for showing results of calculation exhibiting optical characteristics of structures to which the present invention is applied.

FIG. 2 is a graph for showing results of calculation of a relationship between an amount of change of the airgap length and the laser oscillation wavelength of the structure illustrated in FIG. 1 and structures for comparison.

Similarly to the case described with reference to FIG. 5A to FIG. 5C and FIG. 8, a basic structure is a structure with nothing formed at the interface between the gap portion and the semiconductor cavity. An AR film adding structure is a structure in which an AR film is formed at the interface between the gap portion and the semiconductor cavity. A DBR adding structure is a structure in which a DBR as a high reflectivity structure is formed at the interface between the gap portion and the semiconductor cavity. The DBR adding structure is the structure to which the present invention is applied, and the basic structure and the AR film adding structure are the structures for comparison.

Note that, the semiconductor cavity length except for the AR film and the DBR is designed to be $3.25\lambda$, where the center wavelength of 1,065 nm is $1.00\lambda$.

When the results of calculation shown in FIG. 2 are compared with the results of calculation of the structures of a comparative example described above with reference to FIG. 8, a big difference is observed.

In order to clarify the difference, Table 1 is prepared as below in which the wavelength tuning efficiencies of the respective structures are read from the results of calculation shown in FIG. 2 and FIG. 8 and are listed in decreasing order of magnitude.

TABLE 1

| Semiconductor cavity length, interface structure | Wavelength tuning efficiency around center wavelength |
|---|---|
| $3.25\lambda$, DBR adding structure | 0.31 |
| $3.25\lambda$, basic structure | 0.21 |
| $3.25\lambda$, AR film adding structure | 0.12 |
| $3.00\lambda$, AR film adding structure | 0.12 |
| $3.00\lambda$, basic structure | 0.05 |
| $3.00\lambda$, DBR adding structure | 0.015 |

The following can be read from this table.

First, when the semiconductor cavity length is changed from $3.00\lambda$ to $3.25\lambda$, the cavity length increases, but still, the wavelength tuning efficiency of the basic structure is improved.

With regard to the structure in which the basic structure has the AR film added thereto, the following result is acquired. In the case of the related-art semiconductor cavity length of $3.00\lambda$, the wavelength tuning efficiency becomes higher, but, in the case of the structure to which the present invention is applied having a semiconductor cavity length of $3.25\lambda$, in reverse, the wavelength tuning efficiency becomes lower.

On the other hand, with regard to the structure in which the basic structure has the DBR added thereto, the following result is acquired. In the case of the related-art semiconductor cavity length of $3.00\lambda$, the wavelength tuning efficiency becomes lower, but, in the case of the structure to which the present invention is applied having a semiconductor cavity length of 3.25λ, in reverse, the wavelength tuning efficiency becomes higher.

The results can be construed that the wavelength tuning efficiency is changed depending on the semiconductor cavity length and the amount of change thereof varies depending on the reflectivity at the interface between the gap portion and the semiconductor cavity.

This is described in further detail with reference to FIG. 3.

Figure 3:
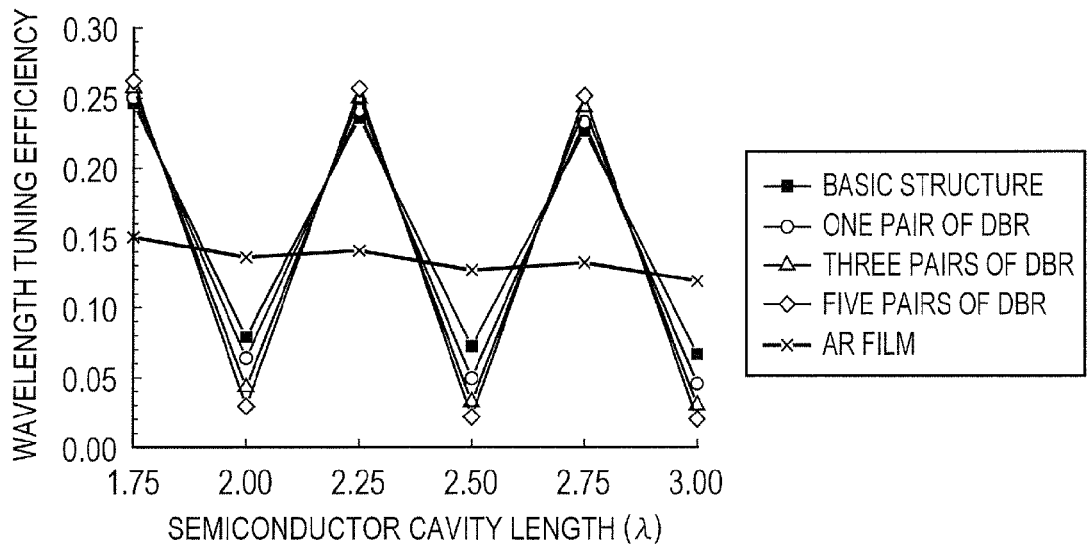
FIG. 3 is a graph for showing results of calculation exhibiting optical characteristics of structures to which the present invention is applied.

FIG. 3 is a graph for showing results of calculation of a relationship between the wavelength tuning efficiency and the semiconductor cavity length when the center wavelength is 1,065 nm with regard to MEMS-VCSELs having various structures.

With regard to the basic structure with nothing formed at the interface between the gap portion and the semiconductor cavity, a structure with a DBR including one pair of layers formed at the interface, a structure with a DBR including three pairs of layers formed at the interface, a structure with a DBR including five pairs of layers formed at the interface, and a structure with an AR film formed at the interface, dependence of the wavelength tuning efficiency on the semiconductor cavity length around the center wavelength of 1,065 nm is calculated.

With reference to FIG. 3, it can be seen that, every time the semiconductor cavity length changes by λ/4, the wavelength tuning efficiency repeats up and down. It can also be seen that, while minute up and down are repeated, as an overall tendency, as the semiconductor cavity length becomes larger, the wavelength tuning efficiency becomes lower.

In this case, with regard to the structure with an AR film, the range of the up and down of the wavelength tuning efficiency as the semiconductor cavity length changes is narrow.

On the other hand, with regard to the structures with a DBR, the range of the up and down of the wavelength tuning efficiency as the semiconductor cavity length changes is wide. Further, as the number of the pairs of layers in the DBR increases, the range of the up and down of the wavelength tuning efficiency becomes wider.

It has hitherto been said that the wavelength tuning efficiency is improved by adding an AR film to the interface between the gap portion and the semiconductor cavity, but only cases in which the semiconductor cavity length is (λ/2)×m have hitherto been reviewed.

It has been made clear by review of the inventors of the present invention that, as described above with reference to FIG. 3, if an AR film is added when the semiconductor cavity length is (λ/2)×m+λ/4, the wavelength tuning efficiency becomes worse in reverse.

In the following, qualitative review of this result is attempted.

A structure for reducing the reflectivity such as an AR film can be understood to have the effect of causing insensitivity to the difference in semiconductor cavity length. Therefore, with regard to any semiconductor cavity length, intermediate characteristics between those of a semiconductor cavity length with which the wavelength tuning efficiency is high when the AR film is formed and those of a semiconductor cavity length with which the wavelength tuning efficiency is low are obtained.

Specifically, in the case of a semiconductor cavity length ((λ/2)×m) with which the wavelength tuning efficiency is originally low, by adding the AR film, the wavelength tuning efficiency can be increased. On the other hand, in the case of a semiconductor cavity length ((λ/2)×m+λ/4) with which the wavelength tuning efficiency is originally high, by adding the AR film, the wavelength tuning efficiency is reduced.

On the other hand, a structure for increasing the reflectivity such as a DBR can be understood to have the effect of causing sensitivity to the difference in semiconductor cavity length. Specifically, in the case of a semiconductor cavity length ((λ/2)×m) with which the wavelength tuning efficiency is originally low, by adding the DBR, the wavelength tuning efficiency is further reduced. On the other hand, in the case of a semiconductor cavity length ((λ/2)×m+λ/4) with which the wavelength tuning efficiency is originally high, by adding the DBR, the wavelength tuning efficiency is further increased.

As a result, from the viewpoint of increasing the wavelength tuning efficiency, a structure having a semiconductor cavity length of (λ/2)×m+λ/4 and having a high reflectivity structure such as a DBR added thereto is most suitable.

In the structure to which the present invention is applied, the semiconductor cavity length is not necessarily required to be strictly equal to (λ/2)×m+λ/4, and a structure in which the semiconductor cavity length is in a certain range around (λ/2)×m+λ/4 can obtain the effect of the present invention. Specifically, it is enough that the semiconductor cavity length is a value that is closer to (λ/2)×m+λ/4 than to (λ/2)×m. In other words, the effect of the present invention can be obtained when the following is satisfied:

$$(\lambda/2)\times m+\lambda/8 < L < (\lambda/2)\times m+3\lambda/8,$$

where L is the semiconductor cavity length, m is an integer of 1 or larger, and λ is the center wavelength of the laser oscillation.

Further, when the following is satisfied, the wavelength tuning efficiency is improved compared with that of the basic structure, which is preferred:

$$(\lambda/2)\times m+7\lambda/40 \leq L \leq (\lambda/2)\times m+13\lambda/40$$

Still further, when the following is satisfied, the range is closer to (λ/2)×m+λ/4, which is more preferred:

$$(\lambda/2)\times m+3\lambda/16 \leq L \leq (\lambda/2)\times m+5\lambda/16.$$

In the structure to which the present invention is applied, the upper reflector and the lower reflector are not specifically limited insofar as the reflectors can obtain a reflectivity that is enough for laser oscillation. For example, a DBR formed of a dielectric or a semiconductor multilayer film, a metal film, or a diffraction grating can be used.

In the structure to which the present invention is applied, it is enough that the high reflectivity structure formed at the interface between the gap portion and the semiconductor cavity increases the reflectivity. For example, a DBR formed of a dielectric or a semiconductor multilayer film, a metal film, or a diffraction grating can be used.

Among them, a DBR formed of a semiconductor multilayer film (so-called semiconductor DBR) is particularly preferred, because of a manufacturing advantage that the DBR can be formed through crystal growth collectively subsequent to formation of the semiconductor cavity, an advantage that, because of the conductivity thereof, current can be diffused to help uniformization of the current injection, and the like.

Further, a DBR formed of a dielectric multilayer film (so-called dielectric DBR) is inferior to a semiconductor DBR in that the DBR cannot be conductive, but is excellent in being able to obtain a refractive index difference that is larger than that a semiconductor multilayer film can, and thus, being able to obtain a high reflectivity with ease. Therefore, depending on a use therefor, there are cases in which a dielectric DBR is more preferred than a semiconductor DBR.

In the structure to which the present invention is applied, as the active layer, one that is used for a commonly-used surface emitting laser can be used. Composition of materials forming the active layer, a thickness of the active layer, and the like can be appropriately selected in accordance with a wavelength at which the laser oscillation is required.

In the structure to which the present invention is applied, for a unit for vertically moving the upper reflector along the optical axis direction, a technology that is commonly used in the field of MEMS can be used. For example, an electrostatic technology, a piezoelectric technology, a thermal technology, an electromagnetic technology, or a fluid pressure technology can be used.

In the structure to which the present invention is applied, the gap portion can be filled with a gas or a liquid, or can be a vacuum. Vacuum as used herein means a negative pressure state, that is, a state in which the air pressure is lower than the standard atmospheric pressure. The calculation herein is performed on the assumption that the gap portion is filled with air and the refractive index is 1.

The surface emitting laser to which the present invention is applied can cause laser oscillation through optical excitation or current injection. In the case of the current injection, it is necessary to form an electrode, but, for the sake of brief description and illustration, such an electrode is omitted herein and the attached drawings.

Further, a plurality of the surface emitting lasers to which the present invention is applied can be arranged on a single plane to be used as an array light source.

Embodiment 2

In Embodiment 2, an application example of a light source device including the surface emitting laser described in Embodiment 1 is described. A wavelength tunable light source device can be used as a light source for optical communication or as a light source for optical measurement. Further, the light source device can be used as a light source device of an information acquisition apparatus configured to acquire information on an inside of an object to be measured in a noninvasive and nondestructive way. In the following, as an example of an information acquisition apparatus using the light source device of this embodiment, an optical coherence tomography apparatus (hereinafter referred to as OCT apparatus) is described with reference to FIG. 4.

Figure 4:
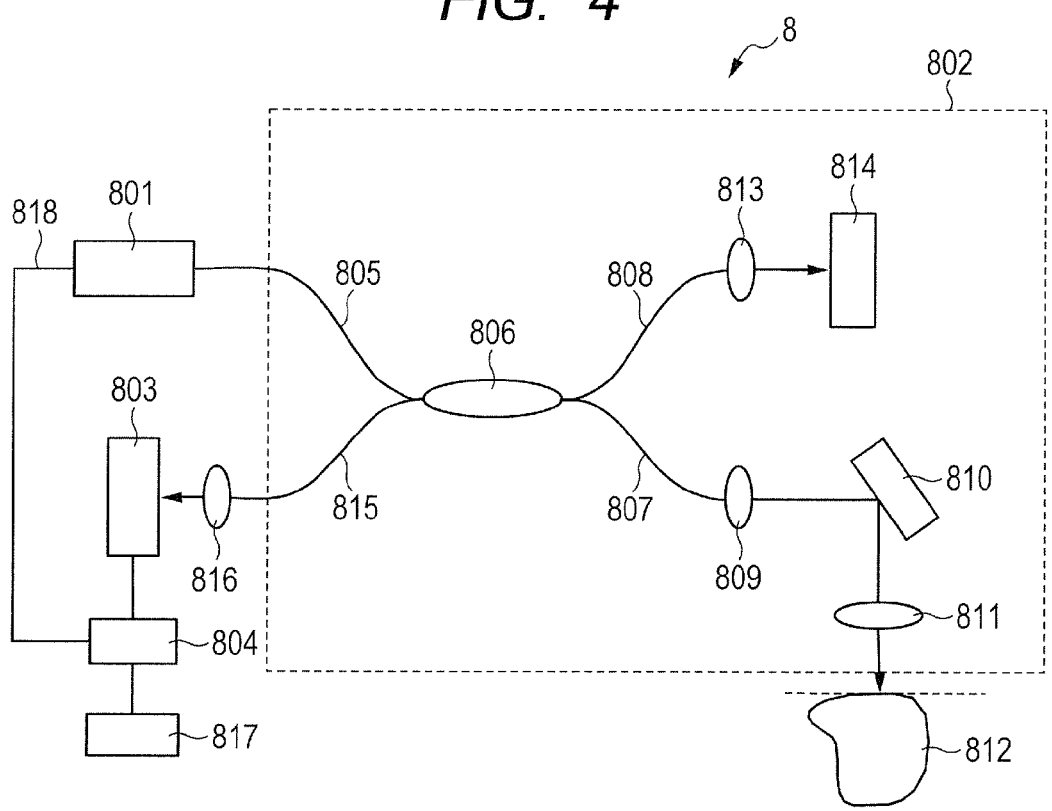
FIG. 4 is a schematic view for illustrating an optical coherence tomography apparatus including the MEMS-VCSEL of the embodiment of the present invention.

FIG. 4 is a schematic view for illustrating an OCT apparatus 8 according to this embodiment. The OCT apparatus 8 includes at least a light source device 801, an interference optical system 802, a light detection portion 803, and an information acquisition portion 804 configured to acquire information on the inside of an object to be measured. As the light source device 801, the surface emitting laser of Embodiment 1 can be used. Further, although not shown, the information acquisition portion 804 includes a Fourier transformer. That the information acquisition portion 804 includes a Fourier transformer herein means that the information acquisition portion 804 has the function of performing a Fourier transform on data inputted thereto, and insofar as the information acquisition portion 804 has the function, no specific limitation is put thereon. An exemplary structure is that the information acquisition portion 804 includes an arithmetic portion and the arithmetic portion has the function of performing a Fourier transform. Specifically, the arithmetic portion is a computer including a CPU, and the computer runs an application having the function of performing a Fourier transform. Another exemplary structure is that the information acquisition portion 804 includes a Fourier transform circuit having the function of performing a Fourier transform.

Light emitted from the light source device 801 passes through the interference optical system 802 to be output as coherent light having information on an object 812 to be measured. The coherent light is received by the light detection portion 803. Note that, the light detection portion 803 may be of a differential detection type or may be a simple intensity monitor type. Information on a time waveform of intensity of the received coherent light is sent from the light detection portion 803 to the information acquisition portion 804. The information acquisition portion 804 acquires a peak value of the time waveform of the intensity of the received coherent light and performs a Fourier transform to acquire information on the object 812 (for example, information on a tomographic image). Note that, the light source device 801, the interference optical system 802, the light detection portion 803, and the information acquisition portion 804 described here can be arbitrarily arranged.

In the following, a process from light emission from the light source device 801 to acquisition of the information on the inside of the object to be measured is described in detail. Light emitted from the light source device 801 passes through a fiber 805, enters a coupler 806, and then, is branched into irradiation light that passes through a fiber 807 for irradiation light and reference light that passes through a fiber 808 for reference light. The coupler 806 operates in a single mode in a wavelength band of the light source, and fiber couplers of various kinds can be 3 dB couplers. The irradiation light passes through a collimator 809 to be collimated light and is reflected by a mirror 810. Light reflected by the mirror 810 passes through a lens 811 to be irradiated to the object 812, and is reflected by respective layers in a depth direction of the object 812.

On the other hand, the reference light passes through a collimator 813 and is reflected by a mirror 814. At the coupler 806, coherent light is generated by the reflected light from the object 812 and reflected light from the mirror 814. The coherent light passes through a fiber 815, passes through a collimator 816 to be condensed, and is received by the light detection portion 803. The information on the intensity of the coherent light received by the light detection portion 803 is converted into electrical information such as a voltage, and is sent to the information acquisition portion 804. The information acquisition portion 804 processes the data on the intensity of the coherent light, specifically, performs a Fourier transform, to acquire information on the tomographic image. The data on the intensity of the coherent light on which a Fourier transform is performed is data sampled at equal wave number intervals in normal cases, but it is also possible to use data sampled at equal wavelength spacings.

The acquired information on the tomographic image may be sent from the information acquisition portion 804 to an image display portion 817 and may be displayed as an image. Note that, by scanning the light with the mirror 810 within a plane perpendicular to an incident direction of the irradiation light, a three-dimensional tomographic image of the object 812 to be measured can be acquired. Further, the light source device 801 may be controlled by the information acquisition portion 804 via an electric circuit 818. Further, although not shown, intensity of light emitted from the light source device 801 may be successively monitored and data thereof may be used to correct an amplitude of a signal for indicating the intensity of the coherent light.

An OCT apparatus is useful in acquiring a tomographic image of an inside of a living body such as an animal or a human in the field of ophthalmology, dentistry, dermatology, and the like. Information on a tomographic image of a living body includes not only the tomographic image of the living body but also a numeric data necessary for acquiring the tomographic image. In particular, it is suitable that an object to be measured be an eyeground, tooth, or blood vessel of a human body and that an OCT apparatus be used to acquire information on a tomographic image thereof.

EXAMPLE

Example of the present invention is described below. Note that, the present invention is not limited to the Example described below. For example, a kind and composition, shape, and size of a material can be appropriately changed within the scope of the present invention.

In the following Example, a case in which the laser oscillation wavelength is around 1,060 nm is described, but operation at an arbitrary wavelength is possible through selecting an appropriate material and an appropriate structure.

Example 1

As Example 1, a VCSEL to which the present invention is applied is described with reference to FIG. 1. FIG. 1 is a schematic sectional view for illustrating a layer structure of the VCSEL in this example.

The VCSEL of this example is formed of a GaAs-based compound semiconductor, and is designed so that a wavelength sweep can be performed around a center wavelength of 1,060 nm.

The upper reflector 100, the gap portion 130, the high reflectivity structure 170, the semiconductor cavity 150 including the active layer 120, the lower reflector 110, and the GaAs substrate 140 are placed in the stated order from the top.

The upper reflector 100 is formed of a DBR in which 36.5 pairs of $Al_{0.4}Ga_{0.6}As$ and $Al_{0.9}Ga_{0.1}As$ that are alternately formed are stacked.

A location of the upper reflector 100 can be vertically changed through an electrostatic force generated by applying a voltage. An electrode for applying the voltage is not shown in FIG. 1.

The gap portion 130 is filled with air, and the length of the gap portion 130 (airgap length) is tunable around 1,600 nm. The high reflectivity structure 170 is, similarly to the upper reflector 100, formed of a DBR in which five pairs of $Al_{0.4}Ga_{0.6}As$ and $Al_{0.9}Ga_{0.1}As$ that are alternately formed are stacked.

The active layer 120 has a multiple quantum well structure in which three cycles of a quantum well layer formed of GaInAs and a barrier layer formed of GaAsP are stacked.

The active layer 120 emits light through current injection. Note that, an electrode for the current injection is not shown in FIG. 1.

The semiconductor cavity length is configured to correspond to around $1.75\lambda$, where the center wavelength of 1,060 nm is $1.00\lambda$.

The lower reflector 110 is formed of a DBR in which five pairs of $Al_{0.4}Ga_{0.6}As$ and $Al_{0.9}Ga_{0.1}As$ that are alternately formed are stacked on stacked thirty pairs of GaAs and AlAs that are alternately formed.

The gap portion 130 of this example is formed using epitaxial growth and selective wet etching. An overview of the process is described.

When epitaxial growth is performed, a film is formed at a portion corresponding to the gap portion as a sacrificial layer of GaAs.

Through the use of a mixture liquid of water, citric acid, and a hydrogen peroxide aqueous solution as an etchant, selective etching can be performed in accordance with an Al composition in AlGaAs. In this example, a mixture in which a citric acid solution, which is a mixture of water and citric acid (at a weight ratio of 1:1), and a hydrogen peroxide aqueous solution at a concentration of 30% are mixed at a ratio of 4:1 (volume ratio) is used as the etchant. This etchant enables selective etching of GaAs and $Al_{0.7}Ga_{0.3}As$, and the gap portion can be formed by removing only the GaAs sacrificial layer.

The high reflectivity structure 170 has a reflectivity of about 60% for light having a wavelength of 1,060 nm, which is higher than the reflectivity at the interface between the gap portion and the semiconductor cavity when the high reflectivity structure is not formed (about 28%). This can increase the wavelength tuning efficiency.

According to the calculation, the wavelength tuning efficiency when the high reflectivity structure 170 is not formed is 0.246. By forming the high reflectivity structure 170 as in this example, the wavelength tuning efficiency can be improved to be 0.262.

As described above, according to the structure to which the present invention is applied, a wavelength tunable surface emitting laser having a more excellent wavelength tuning efficiency than that of a related-art one can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-142912, filed Jul. 11, 2014, which is hereby incorporated by reference herein in its entirety.

What is claimed is:

1. A surface emitting laser, comprising:
a first reflector;
a semiconductor cavity including an active layer; and
a second reflector,
the first reflector, the semiconductor cavity, and the second reflector, which are formed in the stated order,
wherein a gap portion is formed between the first reflector and a semiconductor layer,
wherein a cavity length is tunable,
wherein the surface emitting laser has a high reflectivity structure formed between the gap portion and the semiconductor cavity, and
wherein $(\lambda/2) \times m + \lambda/8 < L < (\lambda/2) \times m + 3\lambda/8$ is satisfied, where L is an optical thickness of the semiconductor cavity after conversion into an optical thickness in a case of no phase change in optical reflection at a first interface that is at a first reflector side of the semiconductor cavity and at a second interface that is at a second reflector side of the semiconductor cavity, m is an integer of 1 or larger, and $\lambda$ is a center wavelength of laser oscillation.

2. A surface emitting laser according to claim 1, wherein the high reflectivity structure comprises a structure in which at least one pair of a high refractive index layer comprising a material that has a relatively high refractive index and a low refractive index layer comprising a material that has a relatively low refractive index are stacked.

3. A surface emitting laser according to claim 1, wherein the high reflectivity structure comprises a distribution Bragg reflector (DBR).

4. A surface emitting laser according to claim 1, wherein the optical thickness L of the semiconductor cavity satisfies $(\lambda/2) \times m + 3\lambda/16 < L < (\lambda/2) \times m + 5\lambda/16$.

5. A surface emitting laser according to claim 1, wherein the optical thickness L of the semiconductor cavity satisfies $(\lambda/2) \times m + 7\lambda/40 \leq L \leq (\lambda/2) \times m + 13\lambda/40$.

6. A surface emitting laser according to claim 1, wherein the optical thickness of the semiconductor cavity comprises an optical path length between an interface of the high reflectivity structure and the semiconductor cavity and an interface between the semiconductor cavity and the second reflector.

7. A surface emitting laser according to claim 1, wherein the semiconductor cavity comprises a stacked body of all semiconductor layers placed between the high reflectivity structure and the second reflector.

8. A surface emitting laser according to claim 1, wherein the high reflectivity structure has a reflectivity of 50% or more at the center wavelength of the laser oscillation.

9. An apparatus, comprising:
a surface emitting laser, comprising:
a first reflector;
a semiconductor cavity including an active layer; and
a second reflector,
the first reflector, the semiconductor cavity, and the second reflector, which are formed in the stated order,
wherein a gap portion is formed between the first reflector and a semiconductor layer,
wherein a cavity length is tunable,
wherein the surface emitting laser has a high reflectivity structure formed between the gap portion and the semiconductor cavity, and
wherein $(\lambda/2)\times m+\lambda/8<L<(\lambda/2)\times m+3\lambda/8$ is satisfied, where L is an optical thickness of the semiconductor cavity after conversion into an optical thickness in a case of no phase change in optical reflection at a first interface that is at a first reflector side of the semiconductor cavity and at a second interface that is at a second reflector side of the semiconductor cavity, m is an integer of 1 or larger, and $\lambda$ is a center wavelength of laser oscillation and
an information acquisition portion configured to acquire information on an inside of an object to be measured.

10. The apparatus according to claim 9, further comprising:
an interference optical system configured to branch light from a light source device into irradiation light to be irradiated to an object to be measured and reference light, and generate coherent light by reflection of light irradiated to the object to be measured and the reference light; and
a light detection portion configured to receive the coherent light,
wherein the information acquisition portion acquires information on the object to be measured based on a signal from the light detection portion.

11. A surface emitting laser, comprising:
a first reflector;
a semiconductor cavity including an active layer; and
a second reflector,
the first reflector, the semiconductor cavity, and the second reflector being formed in the stated order,
wherein a gap portion is formed between the first reflector and a semiconductor layer,
wherein a cavity length is tunable,
wherein the surface emitting laser has a high reflectivity structure formed between the gap portion and the semiconductor cavity, and
wherein $(\lambda/2)\times m+\lambda/8<L<(\lambda/2)\times m+3\lambda/8$ is satisfied, where L is an optical thickness of the semiconductor cavity, m is an integer of 1 or larger, and $\lambda$ is a center wavelength of laser oscillation.

12. A surface emitting laser according to claim 11, wherein the high reflectivity structure comprises a structure in which at least one pair of a high refractive index layer comprising a material that has a relatively high refractive index and a low refractive index layer comprising a material that has a relatively low refractive index are stacked.

13. A surface emitting laser according to claim 11, wherein the high reflectivity structure comprises a distribution Bragg reflector (DBR).

14. A surface emitting laser according to claim 11, wherein the optical thickness L of the semiconductor cavity satisfies $(\lambda/2)\times m+3\lambda/16<L<(\lambda/2)\times m+5\lambda/16$.

15. A surface emitting laser according to claim 11, wherein the optical thickness L of the semiconductor cavity satisfies $(\lambda/2)\times m+7\lambda/40\leq L\leq(\lambda/2)\times m+13\lambda/40$.

16. A surface emitting laser according to claim 11, wherein the optical thickness of the semiconductor cavity comprises an optical path length between an interface of the high reflectivity structure and the semiconductor cavity and an interface between the semiconductor cavity and the second reflector.

17. A surface emitting laser according to claim 11, wherein the semiconductor cavity comprises a stacked body of all semiconductor layers placed between the high reflectivity structure and the second reflector.

18. A surface emitting laser according to claim 11, wherein the high reflectivity structure has a reflectivity of 50% or more at the center wavelength of the laser oscillation.

19. An apparatus, comprising:
a surface emitting laser, comprising:
a first reflector;
a semiconductor cavity including an active layer; and
a second reflector,
the first reflector, the semiconductor cavity, and the second reflector being formed in the stated order,
wherein a gap portion is formed between the first reflector and a semiconductor layer,
wherein a cavity length is tunable,
wherein the surface emitting laser has a high reflectivity structure formed between the gap portion and the semiconductor cavity, and
wherein $(\lambda/2)\times m+\lambda/8<L<(\lambda/2)\times m+3\lambda/8$ is satisfied, where L is an optical thickness of the semiconductor cavity, m is an integer of 1 or larger, and $\lambda$ is a center wavelength of laser oscillation; and
an information acquisition portion configured to acquire information on an inside of an object to be measured.

20. The apparatus according to claim 19, further comprising:
an interference optical system configured to branch light from a light source device into irradiation light to be irradiated to an object to be measured and reference light, and generate coherent light by reflection of light irradiated to the object to be measured and the reference light; and
a light detection portion configured to receive the coherent light,
wherein the information acquisition portion acquires information on the object to be measured based on a signal from the light detection portion.

* * * * *